United States Patent [19]

Brungraber

[11] 3,975,940

[45] Aug. 24, 1976

[54] PORTABLE TESTER FOR MEASURING THE STATIC COEFFICIENT OF FRICTION BETWEEN A FLOOR SURFACE OR THE LIKE AND A SHOE SOLE OR HEEL MATERIAL OR THE LIKE

[75] Inventor: Robert J. Brungraber, Gaithersburg, Md.

[73] Assignee: The United States of America as represented by the Secretary of Commerce, Washington, D.C.

[22] Filed: July 25, 1975

[21] Appl. No.: 599,270

[52] U.S. Cl. ................................................... 73/9
[51] Int. Cl.² ......................................... G01N 19/02
[58] Field of Search ................. 73/9, 104, 105, 159

[56] References Cited
UNITED STATES PATENTS
3,187,552  6/1965  Davies ..................................... 73/9

*Primary Examiner*—Donald O. Woodiel
*Attorney, Agent, or Firm*—Eugene J. Pawlikowski; David Robbins; Alvin J. Englert

[57] ABSTRACT

A portable testing device for determining the static coefficient of friction between a floor surface and a shoe sole or heel material includes an upper, weighted strut movable within a vertical plane and a lower strut pivotably secured to the bottom portion of the upper strut. The upper strut is mounted within a bearing block which is translatably movable within a horizontal plane, and the lower strut has secured to the bottom portion thereof a yoke within which a metal shoe carrying a representative shoe sole or heel material to be tested is pivotably secured. The yoke and shoe project through the base of the device framework so as to rest upon the flooring material being tested, and a trigger is disposed near the shoe so as to be actuated thereby upon the occurrence of slip between the shoe and flooring materials. The trigger is in turn connected to a friction clutch which controls the movement of a graduated rod, which is coupled to the bearing block so as to monitor the movement thereof and upon which the static coefficient of friction data is indicated, and upon the occurrence of slip, the movement of the rod is arrested by the clutch mechanism whereby the friction coefficient may be read directly from the rod.

8 Claims, 2 Drawing Figures

U.S. Patent  Aug. 24, 1976  3,975,940
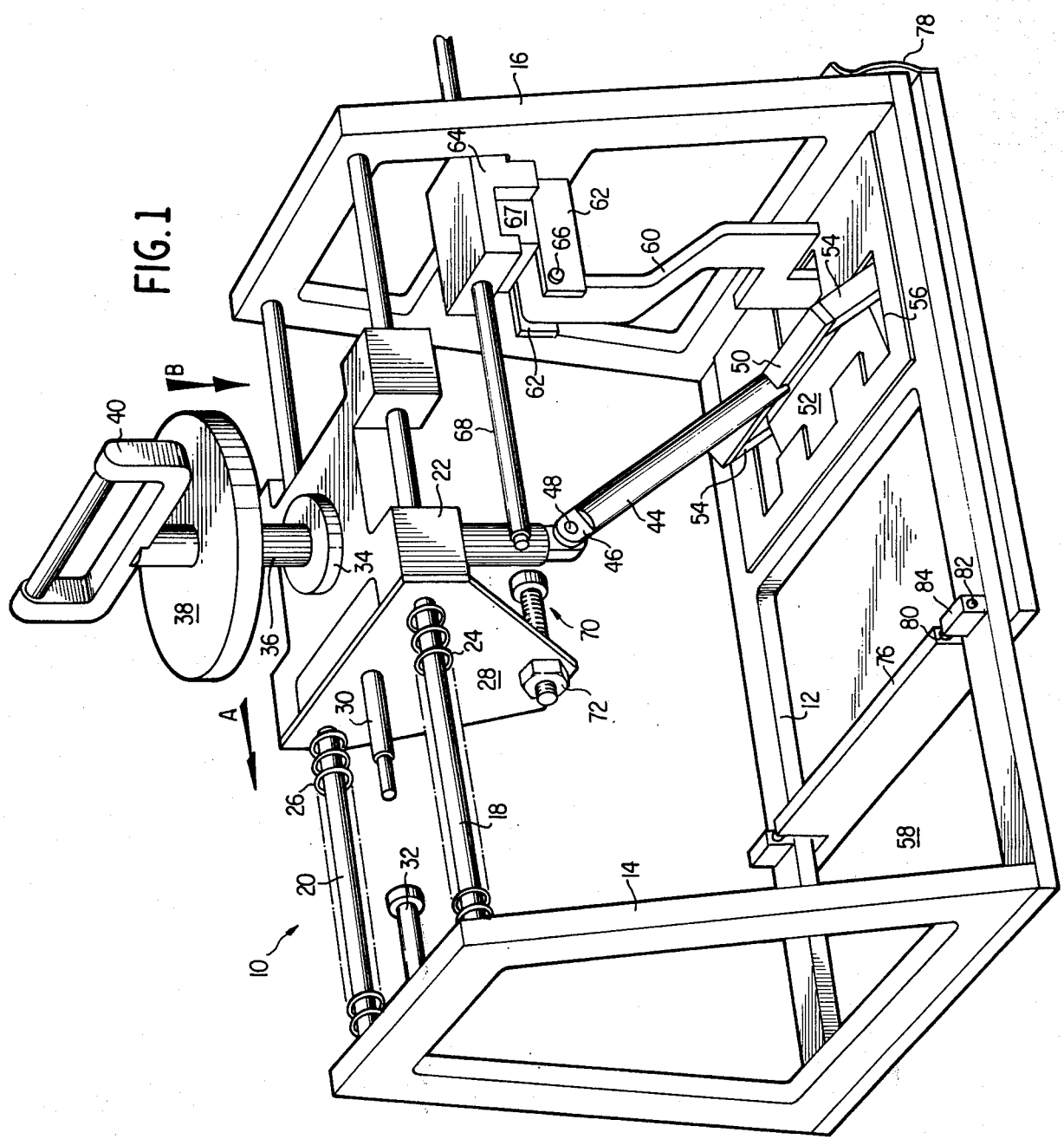
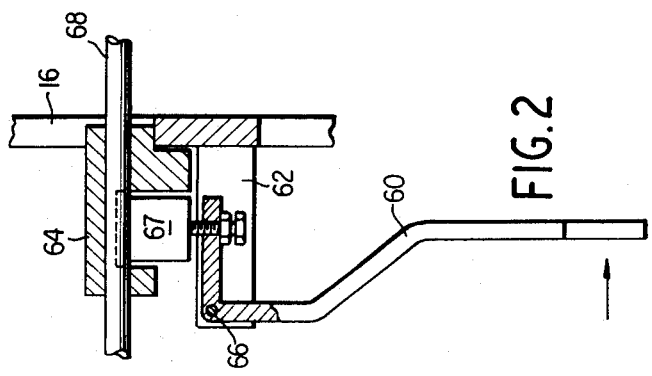

PORTABLE TESTER FOR MEASURING THE STATIC COEFFICIENT OF FRICTION BETWEEN A FLOOR SURFACE OR THE LIKE AND A SHOE SOLE OR HEEL MATERIAL OR THE LIKE

RIGHTS OF THE GOVERNMENT

The invention described herein may be manufactured, used, and licensed by or for the United States Government for governmental purposes without the payment to me for any royalty thereon.

BACKGROUND OF THE INVENTION

1. Field of the Invention

The present invention relates generally to testing apparatus, and more particularly to an improved portable testing apparatus which is able to measure or indicate the static coefficient of friction between a representative flooring surface material and a representative shoe sole or heel material.

2. Description of the Prior Art

One of the best-known and most widely utilized testing apparatus for measuring or indicating the static coefficient of friction between a respresentative flooring surface and a representative shoe sole or heel material is the James Tester Machine which was originally developed by S. V. James of the Underwriters' Laboratories, Inc. The James Machine includes an upper, weighted, rod or strut which is disposed and movable within a vertical plane and to the bottom of which is pivotably connected a lower strut. The lower end of the lower strut has secured thereto a representative shoe sole or heel material and the lower strut-shoe material assembly rests upon a representative flooring sample suitably secured upon a horizontally disposed table which is movable relative to the vertically disposed, upper strut.

In using the machine during performance of a test, the floor sample is placed upon the movable table and the upper and lower strut members, along with the representative shoe material, are positionally adjusted so that the shoe material is in contact with the upper surface of the flooring sample, such contact thereafter being maintained as a result of the weight being constantly impressed upon the upper, vertically movable strut, which weight force is transmitted to the lower strut. The table is moved in a direction relative to the vertical strut such that the angle between the pivotable strut and the vertical plane of the upper strut is varied and increased as the table is moved, and it is thus apparent that the vertical component of force transmitted to, and within, the lower strut is constant, as the superimposed weight is constant, however, the horizontal component of the force is variable, depending upon the angle defined between the lower strut and the vertical plane of the upper strut at a particular moment of time.

A suitable recording mechanism, such as for example, a graphical chart and a recording pencil, is utilized to monitor the relative movement of the table, the chart being secured to the latter and movable therewith while the pencil is secured to the vertical strut, and upon the occurrence of slip, which indicates that the static coefficient of friction between the flooring and shoe sample materials has been reached, the weighted vertical shaft, along with the recording pencil, drops downwardly thereby marking a substantially vertical line upon the chart. The chart includes a graduated scale in terms of the tangent of the angle defined between the hinged and vertical struts, and consequently, the static coefficient of friction is readily indicated.

While it is thus apparent that the James Machine is readily operative and admittedly quite useful in determining the static coefficient of friction between various representative flooring and shoe sole or heel materials, several disadvantages are quite apparent in considering the aforenoted device, particularly the fact that the same is capable of being utilized only in conjunction with material samples. In other words, as a particular floor sample, for example, must be mounted upon the movable table of the device, the Machine is not capable of performing such tests upon installed flooring at field locations. In addition, auxiliary means, either manually or automatically controlled, are necessary for operation of the movable table.

SUMMARY OF THE INVENTION

Accordingly, it is an object of the present invention to provide a new and improved testing apparatus.

Another object of the present invention is to provide an improved testing apparatus which is able to measure or indicate the static coefficient of friction between a representative flooring surface material and a representative shoe sole or heel material.

Still another object of this invention is to provide an improved testing apparatus which is portable and therefore able to indicate the static coefficient of friction between a representative shoe sole or heel material and a representative flooring surface material which is installed in a field location.

Yet another object of the present invention is to provide an improved testing apparatus which is capable of indicating the static coefficient of friction between representative flooring surfaces and shoe sole or heel materials both in field and laboratory locations.

Yet still another object of the present invention is to provide an improved testing apparatus which is automatically actuated and operated without the necessary provision of auxiliary actuating means.

A further object of the present invention is to provide an improved testing apparatus which includes an automatically operated recording mechanism which enables testing personnel to read the static coefficient of friction directly therefrom.

A still further object of the present invention is to provide an improved testing apparatus which is capable of being utilized in conjunction with various flooring surface and shoe materials, such materials being readily selectively interchangeable.

The foregoing and other objectives are achieved according to the present invention through the provision of a portable testing apparatus or tester which includes an upper, weighted rod or strut which is disposed and movable within a vertical plane under the influence of gravity and to the bottom of which is pivotably connected a lower strut. The upper strut is mounted within a bearing support block which is in turn translatably supported within a horizontal plane by means of a standard type frame and the lower end of the lower strut is provided with a suitable yoke and a metal shoe faced on its lower surface with a representative shoe material. The yoke and shoe project through the base of the frame so as to rest upon a representative flooring surface which may either be a sample or an installed floor, and a trigger operatively connected to a friction clutch is disposed near the metal shoe. A graduated rod, for indicating the static coefficient or friction, is slidable within the clutch mechanism and is connected to the bearing block for monitoring the movement thereof, and upon the occurrence of slip between the flooring and shoe materials, the shoe actuates the trigger, and in turn the clutch mechanism, whereby movement of the graduated rod is arrested and the static coefficient of friction of the representative materials may thus be readily ascertained.

BRIEF DESCRIPTION OF THE DRAWINGS

Various other objects, features, and attendant advantages of the present invention will be more fully appreciated as the same becomes better understood from the following detailed description when considered in connection with the accompanying drawings, in which like reference characters designate like or corresponding parts throughout the several views, and wherein:

FIG. 1 is a perspective view of a portable testing apparatus constructed in accordance with the present invention and showing its cooperative parts; and FIG. 2 is a detailed cross-sectional view of the trigger and clutch assembly shown in FIG. 1.

DETAILED DESCRIPTION OF A PREFERRED EMBODIMENT

Referring now to the drawing, there is shown a testing apparatus, generally indicated by the reference character 10, which includes a substantially hollow, rectangular base 12 upon both ends of which are mounted upstanding substantially hollow, trapezoidal standards 14 and 16, and a pair of horizontally disposed rods 18 and 20 have their ends secured within the upper portions of the standards 14 and 16 so as to span the distance therebetween. The rods are coplanar and extend parallel to one another so as to be able to support a substantially square bearing block 22 which is longitudinally translatable thereon, the rods therefore serving as guide rails for the block.

Coil springs 24 and 26, respectively mounted upon those portions of rods 18 and 20 which are interposed between standard 14 and bearing block 22, tend to bias bearing block 22 toward the right, as viewed in the drawing, and consequently, when the bearing block is moved toward the left, as viewed in the drawing and as designated by arrow A, such as for example, during a testing operation, such movement is controlled under the influence of the biasing forces of the coil springs. A vertically disposed, dependent plate 28 is fixedly secured to the left end portion of block 22 and a buffer element 30 fixedly secured to the upper central portion of plate 28, projects laterally from plate 28 and toward standard 14. A stop or stepped rod 32 fixedly secured to the upper central portion of standard 14, similarly projects laterally from standard 14 toward plate 28, and as such elements are also colinearly aligned, the translational movement of bearing block 22 toward standard 14 is arrested upon contact being established between rod 32 and buffer 30.

A bearing member 34 is provided within the central portion of bearing support block 22 and a vertically disposed rod or strut 36 is freely translatable within an axially extending bore, not shown, of member 34. A weight 38, having a circular configuration, is mounted near the upper end of strut 36 so as to continuously move the same downwardly within bearing member 34 under the influence of gravity, as designated by the arrow B. A handle 40, suitable for lifting the entire assembly, is attached to the upper end of strut 36. The lower end of strut 36 is provided with diametrically opposite planar sidewall portions 42 while the upper end portion of another rod or strut 44 is bifurcated so as to provide a pair of fork elements 46, only one of which is shown, elements 46 being pivotably secured to sidewall portions 42 by means of a transversely disposed pin 48. Strut 36 is fluted so as to prevent rotation thereof within bearing 34, and alternatively, strut 36 may be replaced by a pair of spaced shafts which similarly prevent rotation of the strut assembly within the bearing.

The lower end of lower strut 44 has an inverted U-shaped yoke 50 fixedly secured thereto, and a metal shoe 52 having a layer of leather or other shoe sole or heel material (not shown) removably attached to its undersurface by clips, screws, adhesive or other fastening means, is pivotably secured between the dependent leg portions 54 of the yoke. The yoke-shoe assembly 50, 52 projects downwardly through a suitable configured aperture 56 provided within base 12 so as to permit the shoe material to rest upon and be in contact with the flooring material 58 upon which the device 10 is placed, and it should be appreciated that aperture 56 is so configured as to permit strut 44 and the shoe 52 to freely pivot in response to the compound vertically downward and leftward movement of upper strut 36, as will become more apparent hereinafter. In addition, means, not shown, are also provided upon the yoke-shoe assembly so as to operatively cooperate with the interior walls of base 12 defining aperture 56 so as to permit the yoke-shoe assembly to slide and pivot within aperture 56 yet prevents the assembly from falling through aperture 56 when the device is being transported.

A vertically disposed L-shaped trigger 60 is pivotably secured in a dependent manner, between a pair of laterally spaced plates 62 of a friction clutch housing 64 by means of a pin 66, and the lower end of the trigger 60 is disposed adjacent to the shoe 52 so as to be actuated thereby upon the occurence of slip conditions during a testing operation, as will also become more apparent hereinafter. The clutch housing 64 is in turn fixedly secured to standard 16 and a clutch block 67 is threadedly, adjustably supported upon the upper portion of the trigger 60, so as to be disposed within housing 64 and adjacent a horizontally disposed rod 68 translatably supported within housing 64 in the longitudinal direction. A nut bolt assembly, generally indicated by reference character 70, is fixedly secured to the lower portion of plate 28 by suitable nut type fastening means 72 so as to project laterally from plate 28 and extend longitudinally toward rod 68.

The assembly 70 and rod 68 are also colinearly aligned and a disconnectable magnetic coupling is formed between the right end portion of assembly 70 and the left end portion of rod 68. The rod 68 is graduated in terms of the tangent of the angle defined between the lower strut 44 and the vertical plane within which the upper strut 36 is disposed, and consequently, the static coefficient of friction may be read directly therefrom under test conditions. During the testing period, the rod 68 is normally secured to assembly 70 by means of the magnetic coupling defined therebetween and consequently, as the bearing block 22 is moved toward the left, rod 68 is likewise drawn through clutch housing 64 in the same direction, until the occurrence of slip conditions between the flooring and shoe materials. Upon the occurrence of such conditions, the shoe 52 actuates the trigger 60 which in turn causes the clutch block 67 to move upwardly within housing 64, clutch block then preventing further translation of rod 68 whereby the same is disconnected from assembly 70.

As a further alternative, the portable apparatus of the present invention may be converted to a laboratory apparatus by removably securing a plate 74 to the base 12. Plate 74 is spaced below base 12 a sufficient distance to permit a representative floor or shoe sole or heel material tile or block to be inserted between plate 74 and shoe 52 and in order to removably secure plate 74 to base 12, one end thereof is provided with an upstanding flange while the other end thereof is provided with a resilient clip 78. A longitudinal bore 80 is provided within flange portion 76 and a pivot pin, not shown, may be inserted therethrough as well as through bores 82 provided within brackets 84 secured to the upper portion of the base 12 so as to permit pivoting of plate 74 relative to base 12. Upon pivotably securing plate 74 to base 12, the other end thereof may be fixed by means of clip 78 resiliently engaging a suitable shoulder, not shown, provided upon the lower external surface of standard 16.

In utilizing the apparatus for the present invention, the device is initially place upon the flooring surface 58 to be tested and a suitable representative shoe material is secured to shoe 52. The pivotable strut 44 is disposed at a slight angle with respect to the vertical plane of the upper strut 36, as is substantially shown in FIG. 1, the shoe material on shoe 52 being in frictional contact with the floor material 58 to be tested, and it is apparent that the device of the present invention is subsequently automatically operable without the necessity of auxiliary actuating means or devices.

More particularly, the weight 38 causes the upper strut 36 to move downwardly, in the direction of arrow B, under the influence of gravity, such movement in turn tending to cause the yoke-shoe assembly 50, 52 to move toward the right, as viewed in FIG. 1. However, as the static coefficient of friction has not as yet been reached, the shoe material on shoe 52 remains frictionally engaged with the floor material 58, and consequently, a reaction force therefrom causes the bearing block 22 to move translationally toward the left upon guide rails 18 and 20 against the biasing forces of springs 24 and 26, it being of course apparent that such biasing forces are of such magnitude as to control the speed of such translational movement yet not of sufficient magnitude as to prevent such movement.

As the block 22 moves toward the left, and the upper strut 36 continues to move downwardly, the angle defined between lower strut 44 and the vertical plane of upper strut 36 is continually increasing. Concomitantly, the movement of block 22 is also being in effect monitored by means of the graduated rod 68, and when the lower strut achieves an angle relative to upper strut 36 such that the static coefficient of friction between the flooring and shoe materials is overcome and slip occurs therebetween, the shoe 52 will move toward the right and actuate the trigger 60, which in turn actuates the clutch block 67, the latter of which restrains further translational movement of rod 68. The magnetic coupling elements 68 and 70 are then separated and the static coefficient of friction may be read directly from rod 68.

Thus, it may be seen that the portable testing device of the present invention has important advantages over the known prior art structures in that the device is readily useable both within field and laboratory installations for testing flooring samples, as well as installed floor materials, or the like in conjunction with representative shoe materials or the like. In this manner, a variety of shoe materials may be tested for example in conjunction with a particular installed flooring and/or may be tested in conjunction with various floor finishes or polishes applied to such flooring, and it may be therefore be quire apparent that the testing apparatus is quite useful to the flooring, polish, and shoe industries, as well as building maintenance and insurance organizations.

Obviously, many modifications and variations of the present invention are possible in light of the above teachings. It is to be understood therefore that within the scope of the appended claims, the present invention may be practiced otherwise than as specifically described herein.

What is claimed as new and desired to be secured by letters patent of the United States is:

1. Portable testing apparatus for indicating the static coefficient of friction between representative floor surfaces or the like and shoe materials or the like, comprising:
    a base member adapted to be disposed upon one of said representative floor surfaces or the like;
    a first, vertically disposed strut;
    weight means secured upon the upper portion of said first strut for biasing said first strut downwardly under the influence of gravity;
    means for mounting said first strut upon said base so as to permit said strut to move vertically within said plane and also translatably above and parallel to said base, said mounting means and said first strut being automatically movable solely under the influence of the gravitational force of said weight;
    a second strut pivotably connected to the lower portion of said first strut and inclined with respect to the vertical plane of said first strut so as to define an angle therewith, said angle being continuously variable in response to said vertical and translational movement of said first strut;
    yoke and shoe means for securing one of said representative shoe materials or the like to the lower end portion of said second strut, said yoke and shoe means projecting through said base member so as to permit said one of said representative shoe materials or the like to be disposed in contact with said one of said representative floor materials or the like; and
    indicating means operatively associated with said mounting means of said first strut, and said second strut, for indicating said static coefficient of friction in response to the movements of said struts during a testing operation.

2. The apparatus as set forth in claim 1 wherein:
    said inclination of said second strut relative to said plane of said first strut is such as to cause said mounting means and said first strut to be moved in a direction away from said point of contact between said representative materials so as to continuously increase said angle defined between said second strut and said plane of said first strut.

3. The apparatus as set forth in claim 1, wherein said mounting means comprises:
    a bearing block for supporting said first strut within said vertical plane; and guide rails disposed parallel to and above said base member for translatably supporting said bearing block.

4. The apparatus as set forth in claim 3, further comprising:
coil spring means disposed about portions of said guide rails for controlling said translational movement of said bearing block.

5. Apparatus as set forth in claim 1, wherein said indicating means comprises:
a graduated rod containing indicia directly determinative of said static coefficient of friction and connected to said mounting means for movement therewith.

6. Apparatus as set forth in claim 5, further comprising:
a trigger having one end thereof disposed adjacent to said shoe means so as to be moved thereby when said shoe means moves upon the occurrence of slip conditions between said representative materials;
friction clutch means supported above said base member and operatively associated with said rod for controlling the movement of said rod;
said other end of said trigger being pivotably supported upon said friction clutch means for actuating said friction clutch means in response to said movement of said trigger by said shoe means;
said rod being normally freely movable with said mounting means and through said clutch means when said clutch means is not actuated, and being prevented from further movement with said mounting means when said clutch mean is actuated; and
disconnectable means for facilitating the connection and disconnection of said rod to and from said mounting means when said rod is, or prevented from, moving with said mounting means, respectively, under the control of said clutch means.

7. The apparatus as set forth in claim 6, wherein:
said disconnectable means is a magnetic coupling defined between said rod and said mounting means.

8. The apparatus of claim 1, further comprising:
a plate removably secured to and spaced from the bottom of said base and below said yoke and shoe means so as to permit a representative shoe or floor material tile to be inserted between said plate and said yoke and shoe means for testing the same.

* * * * *